US005866383A

United States Patent [19]
Moss et al.

[11] Patent Number: 5,866,383
[45] Date of Patent: Feb. 2, 1999

[54] IN VITRO LIGATION OF FOREIGN DNA INTO LARGE EUKARYOTIC VIRUSES

[75] Inventors: Bernard Moss, Bethesda; Michael J. Merchlinsky, Rockville, both of Md.

[73] Assignee: The United States of America as represented by the Department of Health and Human Services, Washington, D.C.

[21] Appl. No.: 935,812

[22] Filed: Aug. 26, 1992

Related U.S. Application Data

[63] Continuation-in-part of Ser. No. 539,169, Jun. 18, 1990, abandoned, which is a continuation-in-part of Ser. No. 555,811, Nov. 28, 1983, abandoned, which is a continuation-in-part of Ser. No. 445,892, Dec. 1, 1982, abandoned, which is a continuation-in-part of Ser. No. 445,451, Nov. 30, 1982, abandoned.

[51] Int. Cl.$^6$ .......................... C12N 15/00; C12N 15/86; C12N 7/01
[52] U.S. Cl. .................................. 435/172.3; 435/235.1; 435/320.1; 935/32
[58] Field of Search ............................ 435/172.3, 320.1, 435/235.1, 240.2; 935/23, 32, 70, 71

[56] References Cited

U.S. PATENT DOCUMENTS

| | | | |
|---|---|---|---|
| 4,100,267 | 7/1978 | Shaw | 436/516 |
| 4,237,224 | 12/1980 | Cohen et al. | 435/172.3 |
| 4,318,903 | 3/1982 | Lobmann et al. | 424/89 |
| 4,338,296 | 7/1982 | Lubmann et al. | 424/89 |
| 4,348,477 | 9/1982 | Nakano et al. | 435/172.3 |
| 4,419,446 | 12/1983 | Howley et al. | 435/69.1 |
| 4,603,112 | 7/1986 | Paoletti et al. | 435/235.1 |
| 4,722,848 | 2/1988 | Paoletti et al. | 424/89 |
| 4,769,330 | 9/1988 | Paoletti et al. | 435/172.3 |

OTHER PUBLICATIONS

Burand, JP et al. 1980. *Virology* vol 101 pp. 286–290.
Carstens, E.B. et al. 1980. *Virology* vol 101 pp. 311–314.
Crawford, AM. 1989, *J. Gen. Virol.* vol 70 pp. 1017–1024.
Corsaro, B.G. et al. 1989.*J. Virol. Meth.* vol 25 pp. 283–292.
Maclean, A.R. et al. 1987. *J. Gen. Virol.* vol 68 pp. 1165–1171.
Roizman, B. et al. 1985. *Science* vol 229 pp. 1208–1214.
Fenner, F. et al. 1988. *The Poxviruses*, Academic Press, pp. 353–377.
Mackett, M. et al. 1986.*J. Gen. Virol.* vol 67 pp. 2067–2082.
Sam, C.K. et al. 1981. *Ann. Virol. (Inst. Pasteur)* vol 132E pp. 135–150.
Burke, D.T. et al. 1990. *Genet. Anal. Tech. Appl.* vol 7 pp. 94–99.
Sternberg, N.L. 1990. *Genet. Anal. Tech.* Appl. vol 7 pp.126–132.
Scheiflinger, F. et al. 1992. *Proc. Natl. Acad.* Sci. USA vol 89 pp. 9977–9987.
Merchlinsky, M. et al. 1992. *Virology* vol 190 pp. 522–526.
Goebel, S.J. et al. 1990. Virology vol 179, pp. 247–266 and 517–563.

Journal of General Virology (1990) , vol. 71, F. J. Rixon, et al., Insertion of DNA sequences at a unique restriction enzyme site engineered for vector purposes into the genome of herpes simplex virus type 1, pp. 2931–2939.
Science, vol. 236, issued May 1987, D.T. Burke et al., "Cloning of Large segments of exogenous DNA into yeast by means of artificial chromosome vectors", pp. 806–812, see p. 807, figure 1.
Science, vol. 254, issued Dec. 1991, L.J . Ferrin et al., "Selective cleavage of human DNA: RecA–Assisted Restriction Endonuclease (RARE) cleavage", pp. 1494–1497, see pp. 1494–1495 and figure 1.
Virology, vol. 155, issued Sep. 1986, Z. Fathi et al., "Efficient targeted insertion of an unselected marker into the vaccinia virus Genome", pp. 102–103.
Proceedings of the National Academy of Sciences, vol. 81, issued Sep. 1984, M–F. Shih et al., "Expression of Hepatitis B virus S gene by herpes simplex virus type 1 vectors carrying α–and β–regulated gene chimeras", pp. 5867–5870, see p. 5868, figure 1.
Tomic et al, "A rapid and simple method for introducing specific mutations into any position of DNA leaving all other positions unaltered," *Nucl. Acids Res.*18:1656 (1990).
Nakano et al, "Molecular genetics of vaccinia virus: Demonstration of marker rescue," *Proc. Natl. Acad. Sci.* 79:1593–1596 (1982).
Panicalli et al. "Construction of live vaccines by using genetically engineered poxviruses: Biological activity of recombinant vaccina virus expressing influenza virus hemagglutinin," *Proc. Natl. Acad. Sci.* 80:5364–5368 (1983).
Sarver et al. "Bovine papilloma virus deoxyribonucleic acid: a novel eukaryotic cloning vector." *Mol. Cel. Bio.* 1:486–496 (1981).
Moss et al. "Deletion of a 9,000 base–pair segment of the vaccinia virus genome that encodes nonessential polypeptides," *J. of Virology* 40:387–395 (1981).
Panicali et al. "Two major DNA variants present in serially propagated stocks of the WR strain of vaccinia virus," *J. of Virology* 37:1000–1010 (1981).
Weir et al. "Mapping of the vaccinia virus thymidine kinase gene by marker rescue and by cell–free translation of selected mRNA" *Proc. Natl. Acad. Sci.* 79:1210–1214 (1982).
Kur et al. "A novel method for converting common restriction enzymes into rare cutters: integration host factor–mediated Achilles' cleavage (IHF–AC), " *Gene* 110:1–7 (1992.
Ferrin et al. "Selective cleavage of human DNA: RecA–Assisted restriction endonucleases (RARE) cleavage," *Science* 254:1494–1497 (1991).

*Primary Examiner*—Mary E. Mosher
*Attorney, Agent, or Firm*—Knobbe Martens Olson & Bear LLP

[57] ABSTRACT

In a preferred embodiment of the invention, methods are provided for the production of viral vectors from large viral genomes (greater than 50 kbp) that incorporate nucleic acid insertions by direct in vitro ligation. In another preferred embodiment of this invention, viral vectors are provided from large viral genomes. These viral vectors accommodate nucleic acid inserts by direct in vitro ligation and facilitate the expression of foreign protein in eukaryotic cell systems.

19 Claims, 5 Drawing Sheets

FIG. 3A vNotI/lacZ/tk p11 promoter → ATG GTT CGT AAC AAA CGC AAC GAG GCT CTA CGA ATC GGG GAT C|GC GGC CGC|GAT
                Met Val Arg Asn Lys Arg Asn Glu Ala Leu Arg Ile Gly Asp   Arg Gly Arg Asp Arg NotI

FIG. 3B vNotI/tk tk promoter → ATG |GCG GCC GC|C AAC GGC GGA
              Met  Ala Ala Ala  Asn Gly Gly NotI

IN VITRO LIGATION OF FOREIGN DNA INTO LARGE EUKARYOTIC VIRUSES

RELATED APPLICATIONS

This Application is a continuation-in-part of U.S. patent application Ser. No. 539,169, filed Jun. 18, 1990, abandoned, which is a continuation-in-part of Ser. No. 555,811, filed Nov. 28, 1983, abandoned, which is a continuation-in-part of Ser. No. 445,892, filed Dec. 1, 1982, abandoned, which is a continuation-in-part of Ser. No. 445,451, filed Nov. 30, 1982, abandoned. The complete disclosures of all of these prior applications are hereby incorporated herein by reference.

FIELD OF THE INVENTION

This application relates generally to methods for producing viral vectors. More specifically, this invention relates to methods for producing large viral vectors, i.e. greater than 50 kilobase pairs (kbp) that incorporate nucleic acid inserts. In particular embodiments, this invention relates to methods for incorporating large DNA inserts into vaccinia virus vectors.

BACKGROUND OF THE INVENTION

Recombinant DNA technology has made it possible to express genes of one organism within another. The prior art shows that several virus groups, including the papovaviruses, papiluoma viruses, adenoviruses and retroviruses have been employed as eukaryotic molecular cloning and expression vectors. The relatively small sizes of these virus genomes have facilitated the in vitro construction of recombinant DNA molecules. However, these vectors generally exhibit a limited host range, provide severe limitations on the amounts of DNA that can be accommodated and lose their ability to infect subsequent cells upon the insertion of foreign DNA. Genetic engineering using larger viruses, i.e. those having genomes larger than about 50 kbp, such as poxviruses, herpesviruses or baculoviruses, is more difficult because of the large genome size. However, unlike viruses with smaller virus genomes, the larger virus genomes have a greater capacity for accommodating large foreign nucleic acid sequences. Poxviruses are particularly useful because the viruses can infect a wide range of host cells. For poxviruses, such as vaccinia virus, past methods for generating recombinants have employed homologous recombination.

Prior to the present invention, homologous recombination in vivo was used to introduce foreign DNA into the genomes of large DNA viruses such as herpesviruses, poxviruses, and baculoviruses (reviewed by Miller, *Bioessays* 11: 91–5 (1989); Moss, *Science* 252: 1662–7 (1991) and Roizman, et al., *Science* 229: 1208–14 (1985)). Homologous recombination requires a number of genetic manipulations no longer required by the methods disclosed herein. As a first step for practicing homologous recombination, a vector is prepared separate from the viral genome. The vector is preferably a plasmid and in a poxvirus system, the plasmid is modified to contain a poxvirus promoter, sites for insertion of a foreign gene, and poxvirus DNA flanking sequences. A foreign gene is next inserted into the vector to form a chimeric gene and this construct is transfected into cells infected with a poxvirus having sequences complementary to the DNA flanking sequences. The progeny poxviruses are collected and tested for the presence of the foreign gene.

Direct in vitro ligation of DNA, into large eukaryotic viral genomes has not been used. It has heretofore been thought that such ligation techniques are not possible because of the difficulty of working with vector genomes of 50 to 200 kilobase pairs (kbp). With longer DNA molecules there is an increase in the number of times that a particular restriction endonuclease recognition site appears in the molecule and this creates significant problems for vectors created using methods other than homologous recombination. There has been a long felt belief in the scientific community that large genomes of this size are incapable of efficient direct ligation. For example, European Patent Application No. 0 443 335 to Bodemer indicates that the size of the vaccinia genome makes the construction of recombinant genomes by cleavage with restriction endonucleases and subsequent ligation with foreign DNA impossible. Accordingly, homologous recombination methods have been used to insert foreign DNA into viruses having greater than 50 kbp.

There are, however, significant problems associated with homologous recombination. For example, the overall efficiency of homologous recombination is low and the efficiency continues to decline further with increasing insert length. Moreover, the exact site of incorporation of a foreign DNA insert can only be predicted within a given region of the vector genome. The exact site of incorporation varies for each individual recombination event within that given region. For this reason, considerable effort has gone into the development of selection and screening methods. Another potential drawback of homologous recombination protocols is that they generally require an intermediate cloning step followed by propagation of the DNA in bacteria where deletions or rearrangements may occur. Deletions and rearrangements are even more prevalent when the DNA has an unusual structure or is very large. These intermediate plasmid cloning steps make the production of cDNA expression libraries extremely labor intensive.

Recombinant viruses with large genomes, such as vaccinia virus, that have been generated by homologous recombination, have been shown to be useful as vaccines to generate protective immune response against the organisms from which the foreign DNA of the chimeric gene was derived. Some examples of such foreign genes include nucleic acid sequences encoding protein from hepatitis B virus, hepatitis A virus, hepatitis non-A, non-B virus, influenza virus, herpesvirus, cytomegalovirus, adenoviruses, parvoviruses, foot and mouth disease virus, poliovirus, measles virus, rabies virus, coronaviruses, coxsackieviruses and pathogenic bacteria, rickettsia, protozoa, and metazoa.

SUMMARY OF THE INVENTION

The present invention provides methods for generating recombinant viral vectors from eukaryotic viruses with genomes greater than 50 kbp, using direct in vitro ligation. The invention additionally provides methods for generating recombinant viruses with genomes greater than 50 kbp and cells infected by these recombinant viruses. As a preferred example of the application of this invention, a unique restriction endonuclease site was incorporated into the 200,000 bp vaccinia virus genome. Cleavage at this unique restriction endonuclease site produced two viral DNA arms that could be ligated with foreign DNA inserts that preferably encoded protein to produce a chimeric viral genome.

In one embodiment of the present invention, there is provided a method of inserting DNA into the genome of a DNA virus having a genome larger than about 50,000 base pairs. This method includes the steps of obtaining a viral DNA sequence having at least 50,000 base pairs, and cutting the viral DNA sequence at a single restriction endonuclease recognition site using a restriction endonuclease that recognizes the site. Thus, a first viral arm and a second viral arm are created. Insert DNA is obtained and ligated to the viral arms, with a first end of the insert ligated to the first arm and a second end of the insert ligated to the second arm. Preferably, the single restriction endonuclease recognition site is located in a region of the virus that is non-essential for replication of the virus. In certain embodiments, the viral DNA sequence initially includes several of the restriction endonuclease recognition sites in which DNA is to be inserted. If this is the case, the method also includes the step of modifying all but one of the restriction endonuclease recognition sites so that only the one restriction endonuclease recognition site can be cut by a restriction endonuclease recognizing the sites, thereby creating a unique restriction endonuclease recognition site within the viral DNA sequence. This modifying step can be methylation of all of the restriction endonuclease recognition sites but the one restriction endonuclease recognition site into which DNA is to be inserted. The modifying step can also represent an addition, deletion or base change within all of the restriction endonuclease recognition sites but the one restriction endonuclease recognition site. In some embodiments, the modifying step is accomplished by homologous recombination with a DNA sequence containing the addition, deletion or base change. In embodiments where the viral DNA sequence has a unique restriction endonuclease recognition site, the cutting step can be accomplished by complete digestion of the DNA sequence with a restriction endonuclease that recognizes the unique restriction endonuclease recognition site. In an especially preferred embodiment, the unique restriction endonuclease recognition site is located within a marker gene associated with a phenotype, and the method includes the step of identifying viral arms containing insert DNA by identifying a change in the phenotype, such as the development of color. The viral DNA sequence can be a sequence from any of a number of viruses, including a Poxvirus, such as vaccinia virus. In a preferred embodiment, the ligated DNA is transfected into a susceptible host cell. Preferably, the susceptible host cell is infected with a helper virus that enables replication of the transfected DNA. The helper virus can be conditionally lethal to aid in the selection process. In a preferred embodiment of the method, the helper virus does not allow replication of viral DNA in the presence of a functional thymidine kinase gene. Preferably, the transfected DNA can replicate essentially without recombination with the genome of the helper virus. The helper virus can be recombination deficient under at least one condition, such as at a particular temperature, e.g. above 31° C.

Another aspect of the present invention provides a viral vector. This vector includes a DNA sequence having greater than 50,000 base pairs having a marker gene. The sequence also contains a unique restriction endonuclease recognition site within the marker gene and within a region of the sequence that is nonessential for replication of the vector. The marker gene can be a gene coding for a protein, such that the presence of insert DNA in the unique restriction endonuclease recognition site can be detected upon growth of the vector in a susceptible host cell by a change in the expression of the protein. In one embodiment, this protein is viral thymidine kinase. The DNA sequence can include a sequence from one of the following viruses: a Poxvirus, a Herpesvirus or a Baculovirus. In a preferred embodiment, the vector includes sequences from vaccinia virus. In one embodiment, the unique restriction endonuclease recognition site a NotI site. The vector can be provided in a form that is cleaved at the unique restriction site.

Still another aspect of the present invention provides a recombinant viral genome that includes two viral arms and an insert. The insert has greater than about 20,000 base pairs, and the two viral arms together have greater than about 50,000 base pairs. In a preferred embodiment, the viral arms are derived from vaccinia virus. The invention also includes a virus that has a genome as described above, and a host cell containing such a virus.

BRIEF DESCRIPTION OF THE FIGURES

FIG. 3 provides the nucleotide sequences around the NotI sites of vNotI/lacZ/tk and vNotI/tk as determined by DNA sequencing. The nucleotide sequence ATG corresponds to the initiator methionine for the β-galactosidase gene (FIG. 3A-SEQ ID NO: 2) or the thymidine kinase gene (FIG. 3B—SEQ ID NO: 3). The confirmed NotI site in vNotI/lacZ/tk (FIG. 3A—SEQ ID NO: ) or vNotI/tk (FIG. 3B—SEQ ID NO: 13) is also provided.

DETAILED DESCRIPTION OF THE INVENTION

Figure 1:
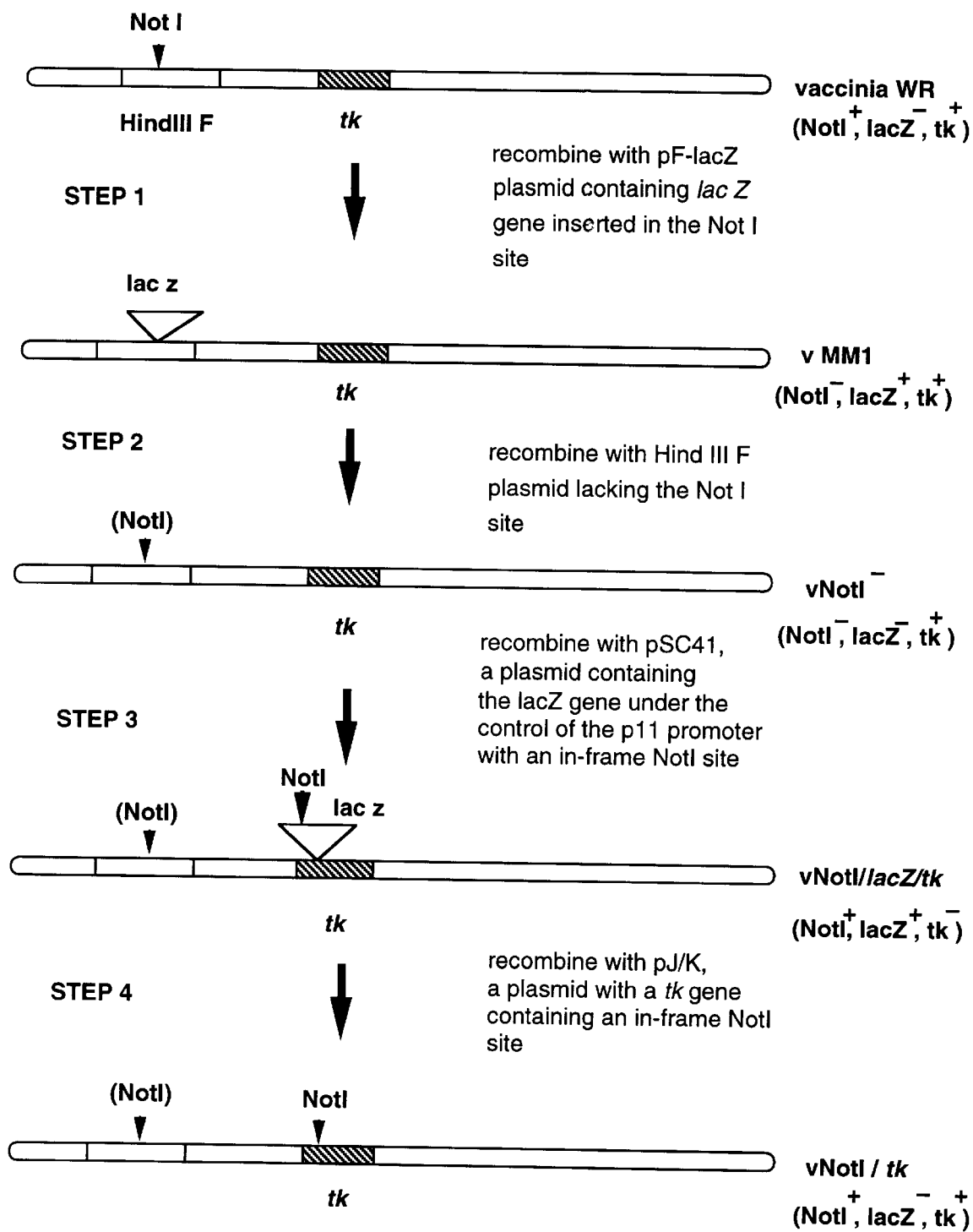
FIG. 1 is a schematic of the strategies employed to generate vaccinia viral vectors vNotI/lacZ/tk and vNotI/tk suitable for direct in vitro ligation. The linear genome of vaccinia virus strain WR is represented in the top figure. Locations of the HindIII F fragment, NotI restriction endonuclease site, and tk gene are indicated.

We have discovered that direct ligation of foreign DNA into large viruses having greater than 50,000 base pairs can be used to create recombinant viruses at high efficiency. Vaccinia is one example of a virus with such a large genome that can be used within the context of the present invention. Considerable research has revealed that the virus contains a linear double-stranded DNA genome with a molecular weight of about 122 million, equivalent to more than 180,000 base pairs. The virus uses its own enzymes for transcription and replication within the cytoplasm of infected cells. For a review of the Poxviridae, and vaccinia virus in particular, see Moss, B. "Poxviridae and Their Replication" in *Fundamental Virology*, Fields, B. N. et al., eds. 1991. Raven Press, New York. Nucleotide sequence data indicate that the transcriptional regulatory signals encoded in the vaccinia virus genome are distinct from those used by eukaryotic cells. Moreover, the virus can accommodate large foreign DNA sequences when the sequences are inserted into nonessential portions of the vaccinia genome. Therefore, vaccinia was selected as a model for generating viral vectors from large viruses that are suitable for direct in vitro ligation.

To circumvent the limitations inherent in the generation of chimeric viral genomes by a homologous recombination protocol, a unique restriction endonuclease site was incorporated into the nearly 200,000 bp vaccinia virus genome.

Cleavage at this unique restriction endonuclease site produces two viral DNA arms that could be ligated with foreign DNA inserts that preferably operably encoded protein to produce a chimeric viral genome.

Direct ligation, to incorporate DNA into large eukaryotic viral genomes, has not previously been reported. In this application, the feasibility of this approach is demonstrated herein through the construction of 2 vaccinia virus vectors using a unique NotI restriction endonuclease site within an integrated copy of the E. coli lacZ gene or the endogenous tk gene. DNA arms, generated by cleavage with NotI, were ligated to foreign DNA fragments and transfected into cells that were infected with a conditionally lethal helper virus. Without special screening or selection, up to 25% of the plaques contained virus with genomic inserts indicating the potential use of this system for the expression of foreign protein from large virus genomes.

Unlike prokaryotic viral cloning strategies, a viral packaging step is not required. Instead, the ligated genome is transfected into cells that express enzymes and factors of the virus core that permit the initiation of transcription and the ultimate assembly of infectious vaccinia virus (Moss, *Virology*: 685–703 (1985), hereby incorporated by reference). In a preferred embodiment of this invention, the in vitro ligation products are transfected into cells infected with a helper vaccinia virus, and more preferably a helper vaccinia virus that is conditionally lethal. In another preferred embodiment of the invention, the vaccinia genome is modified to accommodate a selection system that facilitates the rapid identification of viral plaques containing recombinant virus. As an example of a selection system, "blue-white" color screening is incorporated into one vaccinia expression of this invention (vNotI/lacZ/tk) and thymidine kinase (tk) negative selection is incorporated into another example of a vaccinia virus expression vector (vNotI/tk). While the efficiency of the methods disclosed in this invention are high enough to isolate chimeric viruses by sampling random plaques, the selection options offer a rapid means for identifying candidate recombinant virus.

The term "foreign DNA" or foreign "nucleic acid" is used herein to denote nucleic acid sequence that is not native to a particular location within a vector or genome sequence and has been inserted into the vector, viral or genomic sequence. In a preferred embodiment of this invention, the foreign DNA operably encodes protein.

The term "nucleic acid sequence" or "DNA sequence" is used herein to denote linear fragments of nucleic acid or DNA respectively.

The term "homologous recombination" is a term of art denoting a method or procedure for incorporating a sequence of nucleic acid into a target sequence. For a description of homologous recombination see Moss, B. *Science* 252: 1662–1667 (1991) which is hereby incorporated by reference.

The term "non-essential" is used herein to denote virus nucleic acid sequences that can be removed from the viral genome without altering the infectivity of the encoding virus or the ability of the virus to replicate in tissue culture cells.

The term "viral arms" is used herein to denote the two pieces of nucleic acid obtained by the cleavage of a viral genome at a restriction endonuclease site.

The term "large viral genome" is used herein to denote full length viral genomes greater than 50 kbp.

The term "marker gene" or "marker protein" and "detector gene" or "detector protein" are used interchangeably and denote the gene sequence or protein product of that sequence that facilitates the selection and identification of the presence or absence of the particular sequence in the cell.

The term "phenotype" is used herein to denote the physical characteristics of a given genotype or genotypic arrangement.

Introduction of a Unique Restriction Site into the Candidate Viral Genome

It is anticipated that the methods of this invention will be suitable for any number of eukaryotic viruses with genomes greater than 50 kbp. Examples of viruses contemplated within the scope of this invention include the Poxviruses, including vaccinia virus, and other vertebrate poxviruses as well as insect poxviruses; the Herpesviruses, including Herpesvirus I and II, Cytomegalovirus, Epstein Barr Virus, *Varicella zoster* Virus and the more recently identified Herpesviruses 6 and 7 as well as nonhuman herpesviruses including the primate, bovine and avian herpesviruses; the Iridoviridae and Baculoviruses. The following discussion focuses on the application of this invention in the poxvirus, vaccinia. However, this discussion is not intended to be limiting and those with skill in the arts of virology and molecular biology will be able to adapt the discussion provided below to other virus systems, such as those suggested above.

In a preferred embodiment of this invention, the invention comprises obtaining a viral DNA sequence of at least 50 kbp and cutting the DNA sequence at a single restriction endonuclease recognition site to create two viral arms. These arms are ligated to insert DNA and the resulting construct is used to generate recombinant virus and to express a foreign nucleic acid sequence in a cell. We have demonstrated that very large inserts, e.g. at least 26,000 base pairs, can be accomodated using the methods of the present invention to produce recombinants at high efficiency. This is unlike prior art homologous recombination techniques, in which efficiency of recombination decreased drastically with increasing insert size. It is believed that the efficiency of incorporation of inserts greater than about 20,000 base pairs using prior art homolgous recombination techniques is extremely low. Accordingly, Applicants believe that detection and isolation of recombinant viruses having inserts larger than about 20,000 base pairs using homologous recombination techniques would be so difficult as to be effectively prohibited.

To implement the cloning strategy a unique restriction endonuclease site was identified or incorporated preferably into a non-essential region of the vaccinia virus genome. Restriction endonuclease maps are available from those regions of the vaccinia virus genome that have been sequenced (see Earl et al., *Genetic Maps*: 1.138–1.148 (1990). To test for the presence of a unique restriction endonuclease site in regions of the vaccinia virus genome, not yet sequenced, purified vaccinia virus genome or genome fragments corresponding to the unsequenced portions of the genome, are digested with a candidate unique restriction endonuclease. Digested and undigested fractions are separated by agarose gel electrophoresis and compared. Those with skill in the art of molecular biology will be able to determine the number of restriction endonuclease sites from the resulting nucleic acid separation pattern.

While any unique restriction endonuclease site may be used, those restriction endonucleases that recognize more than 5 nucleotides or have an unusual base composition such as a sequence rich in guanine or cytosine occur at a reduced frequency within a particular DNA sequence and therefore will have a higher probability of being unique to the vaccinia genome. Therefore, it is contemplated that suitable candidate restriction sites contemplated for use in this invention include but are not limited to Csp I, Sac II, Sma I, Eco52 I, NotI, Avr II, Spo I, SSp I or Class IRS enzymes (see Tomic et al., *Nucl. Acids Res.* 18: 1656 (1990), hereby incorporated by reference).

Where a unique restriction endonuclease site is not naturally present within a non-essential portion of the viral genome, or where a unique restriction endonuclease site is located in a location not suited for this invention, it is possible to use techniques known to those with skill in the art, to introduce a unique restriction endonuclease site or to relocate the unique restriction endonuclease site within the viral genome. Similarly, where there are more than one particular restriction endonuclease site it is possible to remove all but one of the sites using site-directed mutagenesis or the like. In a preferred embodiment of this invention the NotI site is selected because the octanucleotide recognition sequence (5'GCGGCCGC 3') is rarely found in DNA and NotI endonuclease digestion generates a 5' overhang of four bases that is easily ligated and, if desired, phosphatased.

Example 1 provides a method for generating a unique restriction endonuclease site within a non-essential portion of a viral genome when more than one of the restriction endonuclease site is present or when the unique restriction endonuclease site is moved from one site in the viral genome to another site. In this method, NotI cut the vaccinia virus genome at a single site within the HindIII F fragment (Earl, et al., *Genetic Maps:* 1.138–1.148 (1990), hereby incorporated by reference). However, the unique NotI site that was used in this invention was designed to be positioned in the open reading frame (ORF) of the marker gene *E. coli* lacZ that was designed to be incorporated into the vaccinia expression vector to detect the presence or absence of foreign gene incorporation. Therefore, Example 1 outlines one method for removing an endogenous NotI site and Example 2 outlines a preferred method for introducing the unique restriction site located within a marker protein into the vaccinia viral genome.

In Example 1, the NotI restriction endonuclease site was removed from the vaccinia genome and replaced with a 4 bp insert using homologous recombination. Since the NotI site was located in a portion of the genome that had not been mapped for open reading frames, it was necessary to first determine if the restriction site was located in an essential region of the genome. Essential portions of the genome are those that include open reading frames or regulatory regions of the genome and are required for virus replication and infection. There are several non-essential portions of the vaccinia genome that have been disclosed in the art. Restriction endonucleases located in these non-essential regions of the vaccinia genome can be modified without disrupting the infectivity of the progeny virus or the ability of the progeny virus to replicate. Examples of such non-essential regions include the thymidine kinase gene and a region of at least 9,000 base-pairs (bp) that is proximal to the left inverted terminal repetition as well as intergenic regions located throughout the genome.

As one method for determining whether or not a particular restriction endonuclease site is located within an essential portion of the genome, a fragment containing the restriction site can be sequenced and the ORF's can be mapped using computer programs known in the art such as those employed by Goebel, et al., *Virol* 179: 517–563, 1990. Alternatively, the open reading frames can be determined manually by searching for ribosome binding sites, start codons, polyadenylation signals and the like. Such signals are well known in the art and disclosed in basic molecular biology texts (see generally Lewin, *GENES IV,* 1990. Oxford University Press, New York).

As another preferred method for determining whether a restriction endonuclease site is located in a nonessential portion of a large viral genome, an insertion cassette, such as a β-galactosidase cassette, can be incorporated into the restriction site, preferably by homologous recombination. As a preferred example, the incorporated cassette includes a region of nucleic acid operably coding for a foreign protein that facilitates the selection of viral genomes. This foreign protein may be a marker protein such as a thymidine kinase, *Escherichia coli LacZ, E. coli* xanthine-guanine phosphoribosyl-transferase (gpt), luciferase or the like.

In a particularly preferred example, a DNA sequence was inserted by homologous recombination into the NotI restriction endonuclease site located in the HindIII F fragment. This DNA sequence consisted of the vaccinia virus P11 promoter derived from the gene encoding the 11K structural protein (Wittek, et al., *J. Virol* 49: 371–378 (1984), hereby incorporated by reference) regulating the *Escherichia coli* lacZ gene. FIG. 1 is a schematic outlining a preferred strategy for the production of two vaccinia expression vectors vNotI/lacZ/tk and vNotI/tk suitable for in vitro ligation to a foreign nucleic acid insert following NotI digestion. Step 1 illustrates the viral genome before and after homologous recombination using the plasmid pF-lacZ containing the P11-lacZ gene cassette derived by digestion of pSC20 (Buller et al., see Example 1) with Bgl II in the NotI site of the HindIII F fragment. β-galactosidase activity was used as a marker for recombinant virus selection and Southern analysis of DNA obtained form the virus plaques using lacZ gene fragments as probes confirmed the identity of the positive clones. A clone, vMM1, was selected that had the lacZ gene inserted into the NotI site as illustrated in FIG. 1. The ability to isolate a recombinant vaccinia virus containing an insert at the NotI site implied that the DNA immediately surrounding this restriction site was not required for replication. This region, HindIII F, was then sequenced and it was confirmed that the NotI site was in a region not required for protein expression (Goebel et al., see Example 1). Such methods can similarly be used by one of skill in the art, to determine whether or not a particular region of nucleic acid from any large virus genome (>50 kbp) is essential to progeny virus production.

After determining that the NotI site was non-essential to progeny virus production, the NotI site was eliminated by replacing the site with an identical HindIII fragment that had the NotI site removed, as described in Example 1. Methods for cleaving nucleic acid at a restriction site, filling in the overhanging ends and religating the filled in ends are well known to those with skill in the art of molecular biology and these methods can be located in a molecular biology methods handbook, such as Maniatis, Fritsch and Sambrook, *Molecular Cloning, a Laboratory Manual,* Cold Spring Harbor Laboratory (1982). The resulting NotI negative (NotI⁻) viral genome was tested by restriction enzyme analysis with NotI and by Southern DNA blotting of the viral DNA to confirm the loss of the lacZ gene as well as the NotI site. An illustration of the viral construct containing the 4 bp insert is provided in FIG. 1, step 2 as vNotI⁻.

Similar results can be obtained using any number of methods known in the art for deleting, substituting or adding base pairs within a particular restriction endonuclease site. Thus, restriction fragments from a large viral genome that contain a restriction site to be modified can be isolated after fragment separation on an agarose gel. The fragment can be incorporated into a working plasmid such as pBluescript (Stratagene, LaJolla, Calif.) or the like and the restriction site can be modified by oligonucleotide selection employing the polymerase chain reaction or by any number of site-directed mutagenesis strategies known to those in the art. The modified fragment is then incorporated into a suitable vector and introduced into the large viral genome by homologous recombination.

Other methods additionally contemplated within the scope of this invention for modifying a particular restriction endonuclease site such that it is no longer recognized by its restriction endonuclease include methylating all the restriction endonuclease recognition sites but one. For procedures for modifying a particular restriction endonuclease site by methylation see Ferrin, et al. (*Science* 254: 1494–1497, 1991) and Koob, et al. (*Gene* 110: 1–7, 1992), which are both hereby incorporated by reference.

An alternative procedure for the generation of sequence-specific changes in the vaccinia virus genome is the use of transplacement by transient dominant selection (Spyropoulos et al, *J. Virol* 65: 4609–4618, 1991). Homologous DNA recombination within cells infected with vaccinia virus with a plasmid containing an altered portion of the genome within homologous sequences and a selectable marker, such as the bacterial xanthine-guanine phosphoribosyl-transferase (gpt) gene, will generate genomes containing two copies of the homologous portion of the genome by a single crossover event. After the removal of selective pressure, another single crossover event between the duplicated sequences results in the excision of the plasmid sequences, including the selectable marker gene, and one of the copies of the homologous portion of the genome. The viral genomes will contain either the altered or wild type sequence. By appropriate screening (such as Southern blotting of restriction digests of viral DNA) one can identify which viral stock contains the desired alteration in sequence. This DNA replacement procedure can be used to generate sequence alterations anywhere within the viral genome.

INSERTION OF UNIQUE RESTRICTION ENDONUCLEASE SITE INTO MARKER PROTEIN

In a preferred embodiment of this invention, the unique restriction site is preferably inserted into a suitable marker or detector protein. Inactivation of the detector protein by the incorporation of a foreign nucleic acid insert into the unique restriction site serves as a selectable marker for the isolation of recombinants. However, the inclusion of the unique restriction site into a marker protein is designed to reduce the screening effort required to identify a positive clone. Those with skill in the art will recognize that a marker protein is not required to generate or identify chimeric viral genomes. Techniques such as DNA nucleotide sequencing, Southern hybridization or the like could similarly be used to identify insert positive clones.

There are a number of marker proteins or detector proteins that could be used by those with skill in the art to readily identify viral plaques containing insert. Possible marker or detector proteins contemplated for use in this invention include but are not limited to thymidine kinase, *Escherichia coli LacZ*, *E. coli* xanthine-guanine phosphoribosyl-transferase (gpt), luciferase or the like. Selection methods are particularly useful when only a small amount of insert DNA is available or when the object is to prepare a library of recombinant viruses. Two specific examples of the use of marker proteins are provided here. In one embodiment the unique restriction endonuclease site is incorporated into the open reading frame of the lacZ gene and in another preferred embodiment the NotI site is incorporated into the open reading frame of a thymidine kinase (tk) gene. Viral vectors generated by the methods of this invention are particularly well suited for library construction.

The construction of the vaccinia virus vector, vNotI/lacZ/tk, involved the location and elimination of an existing NotI site in the vaccinia virus genome, followed by the incorporation of a cassette containing a vaccinia virus promoter regulating the NotI/lacZ gene. This cassette was inserted into a non-essential locus, such as the tk gene, within the vaccinia virus genome. This step is diagramed in FIG. 1, Step 3.

This step was accomplished using homologous recombination involving the transfection of plasmid pSC41, an intermediate in the construction of pUV1 (Falkner et al., see Example 2), containing the tk gene interrupted by a cassette consisting of a P11 promoter-lacZ gene with an in-frame NotI site at the fifteenth codon. Because of the anticipated tk⁻ phenotype, 5-bromodeoxyuridine (BUdR) was used in conjunction with tk⁻ cells for selection of recombinant virus plaques (Earl et al., *Current Protocols in Molecular Biology* ("*Current Protocols*"), 16.15.1–16.18.10, 1990, hereby incorporated by reference, and Example 2). In additional X-Gal staining confirmed that the β-galactosidase fusion protein was active. One such NotI+, lacZ+, tk⁻ recombinant virus, named vNotI/lacZ/tk, was purified and amplified.

Figure 2A:
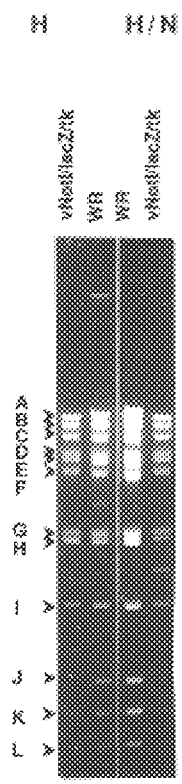
FIG. 2 provides photographs of agarose gels containing vaccinia viral vectors vNotI/lacZ/tk and vNotI/tk, together with vaccinia vaccine strain WR, digested with HindIII or HindIII and NotI to confirm the presence of the unique NotI site within the HindIII F fragment.

The position of the unique restriction site was confirmed by restriction digestion and agarose gel electrophoresis as well as by DNA sequencing. FIG. 2A is a photograph S of the electrophoretic pattern of vNotI/lacZ/tk and vNotI/tk digested with HindIII (H) or HindIII and NotI (H/N). The mobility of the HindIII fragments is altered, as predicted, by NotI digestion indicating the presence of a unique NotI site in the digests. This electrophoretic pattern of the recombinant virus genome confirmed the position of the NotI site within the lacZ gene. DNA nucleotide sequence analysis of this region produced the sequence provided in FIG. 3A and verified the incorporation of the NotI site in the lacZ open reading frame.

Cleavage of the unique restriction endonuclease incorporated into the virus genome results in the production of viral arms that can be directly ligated to a DNA fragment with NotI compatible ends. Religated vector will generate intact marker protein while incorporated foreign protein generates inactive marker protein. vNotI/lacZ/tk uses lacZ as its selectable marker. Loss of β-galactosidase activity upon plaque assay with the chromogenic substrate X-gal (5-bromo-4-chloro-3-indolyl-β-D-galactopyranoside, Boehringer Mannheim, Indianapolis, Ind.) results in a phenotypic change from blue to white plaques. White plaques are those containing insert while blue plaques indicate vector religation.

Figure 2B:
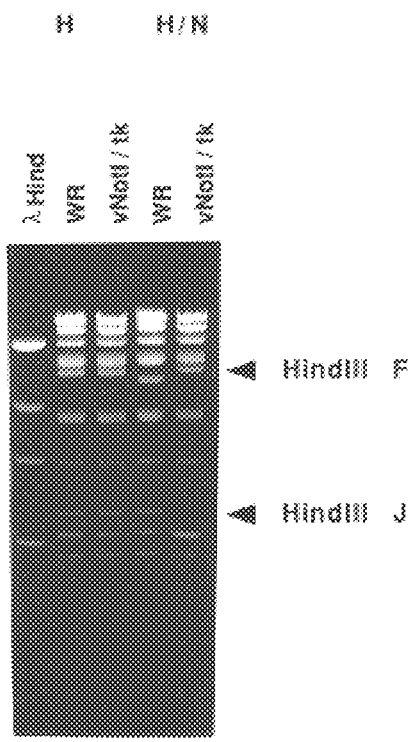

A second exemplary vector suitable for direct in vitro ligation was constructed based on thymidine kinase selection. The second vector, vNotI/tk, permits direct cloning of NotI fragments into vaccinia virus and selection for tk⁻ cells. As disclosed in Example 1 and illustrated in FIG. 3B, a unique in frame NotI site was engineered using homologous recombination to introduce the tk gene containing a NotI site immediately after the tk translation initiation codon. Using methods identical to those described for the production of vNotI/lacZ/tk, the resulting plasmid was transfected into cells that had been infected with vNotI/lacZ/tk. In contrast to the latter virus, which is lacZ⁺ and tk⁻, the new recombinants were expected to be lacZ⁻ and tk⁺. tk⁻ cells were grown in HAT medium (Weir et al., see Example 2) to specifically select tk⁺ virus plaques, see Example 4. DNA from a tk⁺ plaque isolate was analyzed by restriction endonuclease analysis and the resulting electrophoretic pattern of the digest is provided in FIG. 2B and confirmed by DNA sequencing (FIG. 3B).

The exemplary viral vectors provided in FIG. 1 contain one unique restriction endonuclease site. The incorporation of foreign nucleic acid inserts ending in NotI compatible sites into the viral vector results in the ligation of inserts in a number of different orientations. One orientation that was selected by DNA sequencing is provided in FIG. 1. In addition, other recombinants will included inserts in the reverse orientation or inserts consisting of NotI inserts ligated in tandem. It is contemplated that different orientations may be suitable for different applications involving different levels of protein expression. The orientation of the insert can be readily confirmed by those with skill in the art using DNA sequencing or the like.

It is additionally contemplated that a second unique restriction endonuclease site can also be incorporated into the viral vector preferably downstream from the first unique restriction site and still more preferably also within the marker protein. Incorporation of the second restriction endonuclease site into the vector provides a method for directed insert incorporation using inserts with ends complementary to the restriction endonuclease. The presence of two restriction endonuclease sites is particularly useful for the incorporation of an insert in a defined orientation. Still further, it is also contemplated that the viral vector may incorporate multiple cloning sites within a suitable marker protein to facilitate the insertion of a variety of restriction endonuclease fragments.

Use of the Vaccinia Vectors vNotI/LacZ/Lk and vNotI/tk to Express Foreign Protein in a Cell The viral vectors vNotI/lacZ/tk and vNotI/tk were used to incorporate foreign nucleic acid sequences into virus genomes and to facilitate the introduction of large foreign nucleic acid sequences into cells. The DNA was purified from viruses vNotI/lacZ/tk or vNotI/tk and cleaved with NotI to produce vector arms of approximately 40 and 150 kbp. In separate experiments, two different size foreign DNA fragments with NotI ends were ligated to the vaccinia virus DNA arms. The first was a 4.3 kbp fragment obtained from pNot, a plasmid produced by digestion of pBR322 with HindIII, followed by treatment with the Klenow fragment of DNA polymerase to fill in the recessed ends and ligation of the treated fragment to NotI linkers. The second fragment was 26 kbp and was obtained from pBHL, a plasmid containing the HindIII B and L fragments from *Varicella zoster* virus (Davison et al., see Example 7) cloned into plasmid pTR262 (Roberts et al., see Example 7). This plasmid contains a single NotI site within the *Varicella zoster* coding sequence.

The plasmids were digested with NotI, ligated separately to the vaccinia virus DNA arms and precipitated with calcium phosphate. The precipitated DNA was applied to monolayers of CV-1 cells that were infected with ts42, a conditionally lethal temperature sensitive vaccinia virus mutant, that is defective in DNA replication (Condit et al., Sridhar et al., and Traktman et al., see Example 7) and homologous recombination at 40° C.

Helper viruses are those viruses that together with the transfected nucleic acid provide appropriate proteins and factors necessary for replication and assembly of progeny virus. Conditionally lethal helper virus was previously used to facilitate the isolation of viruses with genomes formed by homologous recombination between co-transfected plasmid and wild type DNA (Fathi, et al., *Virol* 155: 97–105 (1986) and Kieny, et al., *Nature* 312: 163–166 (1984), both hereby incorporated by reference). Incubation of ts42 infected cells transfected with the constructs of this invention and incubation at 40° C. prevents recombination between the helper virus and the recombinant viral vector. Following infection, the cells were incubated until progeny virus was produced and the cells were harvested. The virus titer was determined by plaque assay on cell lines at 37° C.

The progeny from experiments using vNotI/tk were inoculated at 37° C. either on BSC-1 cells in regular medium or tk⁻ cells in selective medium since vNotI/tk virus with insert in the NotI would inactivate the tk gene and the resulting virus would have a tk⁻ phenotype allowing plaque selection in the presence of BUdR. In contrast, virus formed by religation of the arms or from helper virus would be tk⁺ and would not be able to form plaques under the selection conditions. Without selection, approximately ⅓ to ¼ of the clones contained the appropriate insert. With selection, all plaques tested contained the correct insert. NotI/HindIII double digests of DNA samples from cells infected with virus derived containing the fragment isolated under BUdR selection were analyzed by Southern blotting and the results are provided in FIG. 4. The samples were electrophoresed through a 1.0% agarose gel, transferred to a nylon membrane (Nitrocellulose, Schleicher and Schuell) and probed by Southern blot hybridization (see Example 5) using pBHL DNA labeled with $^{32}P$ by random primer extension (Pharmacia, Piscataway, N.J.). Hybridization probes indicated that the entire insert from pBHL had been stably integrated into the vaccinia virus genome. These results were confirmed by the electrophoresis of full length viral genomes through agarose gels. The increased size of the recombinant virus in lanes 1–5 was compared to control virus (WR) (FIG. 5). In each case the DNA was larger than the 200,000 bp wild type vaccinia virus WR genome, and the difference in size was consistent with the insertion of an additional 26 kbp of DNA.

The transfection mix derived from vNotI/lacZ/tk was analyzed by plaque assay on BSC-1 cells at 37° C. Colorless plaques produced in the presence of the chromogenic substrate X-gal were selected to contain potential vector recombinants containing insert. Inserts were verified by restriction endonuclease analysis and Southern transfer using methods previously described. The absence of the NotI site in the HindIII F fragments of the chimeric genomes and the absence of a temperature sensitive phenotype argue against recombination between transfected and helper virus DNA. For the small and large DNA fragments, approximately 300 and 100 colorless and 30 and 100 BUdR resistant plaques were obtained per microgram of vNotI/lacZ/tk or vNotI/tk DNA, respectively. Thus, vNotI/lacZ/tk and vNotI/tk are a pair of useful vectors providing either BUdR selection or blue-white screening for the introduction of large DNA fragments into the vaccinia virus genome by non-recombinational methods.

There are a variety of modifications that will now be evident to those of skill in the art that can be incorporated into the methods of this invention to improve the frequency of insert positive vector. For example, it is possible that the number of insert positive constructs could be increased even further by phosphatase treating the ends of the vector to prevent self-ligation. Phosphatase treatment may be particularly useful where selection systems are not feasible. However, strong selection systems such as screening for the inability of the viral progeny to synthesize β-galactosidase translating into a white phenotype, or selecting for progeny production in the presence of BUdR (tk⁻ phenotype), resulted in the production of plaques universally containing virus with inserts.

As another modification contemplated within the scope of this invention, the recombinant vaccinia genome is transfected into packaging cell lines constitutively expressing vaccinia virus protein traditionally supplied by helper virus such as ts42. Such packaging cell lines are available for a variety of retroviral vectors and it is anticipated that the application of similar techniques to vaccinia susceptible cells under appropriate selection conditions would result in suitable packaging cell lines.

This invention, advantageously provides a method for easily inserting large DNA fragments into large viral genomes. Insertion of large DNA fragments is difficult by homologous recombination. However, using the methods of this invention, the efficiency of incorporating a 26 kbp insert was similar to the efficiency of incorporating a 4.3 kbp insert using the methods of this invention. This level of insert efficiency is not available by homologous recombination. The size of the insert incorporated into large viral genomes, such as the Poxviruses and the Herpesvirus family may only be limited by the physical constraints of virus assembly on the genome size. A large drop in efficiency was noted when a DNA fragment approaching 50 kbp was used in the vaccinia system. If the packaging capacity is the limiting factor to insert size, use of vaccinia virus deletion mutants (Perkus, et al., *Virology* 180: 406–410 (1991), hereby incorporated by reference) should allow the limit to be increased another 25 to 50 kbp.

The vectors provided in this invention permit expression from the fusion protein using the weak early tk promoter located in the vNotI/tk construct or expression from the strong late P11 promoter of vNotI/lacZ/tk. Other levels of expression could be achieved by inserting the foreign sequence as part of a promoter-gene cassette. Additional refinements of the vectors, known in the art, are similarly contemplated to permit enhanced expression or permit other modes of selection.

An exemplary method for generating recombinant Herpesvirus vectors suitable for direct in vitro ligation is provided in Example 8. Once the vectors are produced, it is contemplated that any number of inserts containing nucleic acid sequence operably encoding protein, can be produced and transfected into permissive cell lines to generate progeny virus, see Example 9. The virus is useful for expressing foreign protein in cells or for delivery a particular gene sequence to a cell. The viral vectors produced using the methods of this invention are particularly suited for vaccine development and those with skill in the art will be able to test the resulting viruses as candidate vaccines.

Particular embodiments of the invention will be discussed in detail and reference will be made to possible variations within the scope of the invention. There are a variety of alternative techniques and procedures available to those of skill in the art which would similarly permit one to successfully perform the intended invention.

EXAMPLE 1

Identification of a Non-essential Portion of the Viral Genome and Removal of a Restriction Endonuclease Cleavage Site Step 1 illustrates the viral genome before and after homologous recombination using the plasmid pF-lacZ containing the P11-lacZ gene cassette derived by digestion of pSC20 (Buller, et al., *J. Virol* 62: 866–874, 1988 hereby incorporated by reference) with Bgl II in the NotI site of the HindIII F fragment. The progeny were analyzed by plaque assay (see *Current Protocols.* p. 16.16.5). Plaques that turned a blue color with X-Gal were isolated and expanded (see *Current Protocols.* pp.16.17.12–16.17.13).

Restriction enzyme and DNA blot analysis (see Maniatis et al., supra) of DNA from one purified recombinant virus, vMM1, had the lacZ gene inserted into the NotI site as depicted in FIG. 1. The ability to isolate such a recombinant vaccinia virus indicated that the DNA at the NotI site was non-essential. Subsequent sequencing of the HindIII F fragment of vaccinia virus strain Copenhagen (Goebel, et al., *Virol* 179: 517–563, 1990, hereby incorporated by reference) indicated that the NotI site is in an intergenic region.

Since the NotI site was non-essential, it was eliminated from vMM1 by homologous recombination with a plasmid containing the HindIII F fragment that had been cut with NotI and the recessed ends filled in with the Klenow fragment of DNA polymerase prior to re-ligation (see Maniatis, supra) (FIG. 1, step 2). Successful recombination resulted in a replacement of the P11 promoter-lacZ cassette with a 4 bp insertion that destroys the NotI site (for homologous recombination methods see *Current Protocols* pp. 16.17.1–16.17.6) These recombinants could no longer express β-galactosidase, therefore, colorless plaques were picked from monolayers that also contained parental-type plaques that stained blue with X-Gal. Restriction enzyme analysis and DNA blotting of the viral DNA of vNot- confirmed the loss of the lacZ gene and the NotI site. (see Maniatis et al., supra and *Current Protocols.* pp. 16.18.3–16.18.4)

EXAMPLE 2

Incorporation of a Marker Gene Containing a Unique Restriction Endonuclease Site Into a Non-Essential Portion of the Viral Genome Once the original NotI site was removed from the vaccinia virus genome, the lacZ gene was incorporated with an internal NotI site located in frame in the tk locus (see FIG. 1, step 3). Transfection was carried out with plasmid pSC41, an intermediate in the construction of pUV1 (Falkner, et al., *Nuc Acids Res.* 15: 7192, 1987 hereby incorporated by reference), which contains the vaccinia virus tk gene interrupted by a cassette consisting of a P11 promoter-lacZ gene with an in-frame NotI site at the fifteenth codon. Transfection procedures are detailed in Example 3. Because of the anticipated tk⁻ phenotype, 5-bromodeoxyuridine (BUdR) was used in conjunction with tk⁻ cells for selection of recombinant virus plaques (see Example 3 and *Current Protocols* 16.15.1–16.18.10, 1990). In addition, X-Gal staining resulted in blue plaques and confirmed that the β-galactosidase fusion protein was active. One such NotI+, lacZ+, tk⁻ recombinant virus, vNotI/lacZ/tk, was purified and amplified using methods described in *Current Protocols*. The structure of the virus genome was confirmed by restriction enzyme analysis (FIG. 2A) and the position of the NotI site within the lacZ gene is provided in FIG. 3A.

A second vector, vNotI/tk, was constructed for the direct cloning of NotI fragments using selection in tk– cells. As indicated in FIG. 1 and provided in FIG. 3B, a unique in frame NotI site was engineered immediately after the translation initiation codon of the tk gene using and the resulting plasmid pJ/K was transfected into cells that had been infected with vNotI/lacZ/tk. Plasmid pJ/K was constructed by mutagenizing an m13 clone containing the sequences corresponding to the vaccinia tk gene with the oligonucleotide 5'ATGTCCGCCGTTGGCGGCCGCCATGAT-GACAATAAA 3' (SEQ ID NO: 1) (Zoller, et al., *DNA* 3: 479–488, 1984 hereby incorporated by reference) and replacing the sequences from a plasmid containing the leftmost portion of the HindIII J fragment from the HindIII site to the ClaI site found in the vaccinia tk gene with the corresponding fragment derived from the double-stranded RF (replicative form) form of the m13 DNA (see Zoller, et al., *DNA* 3: 479–488, 1984, supra).

In contrast to the vNotI/lacZ/tk virus, which is lacZ$^+$ and tk$^-$, the new recombinant virus vNotI/tk was lacZ$^-$ and tk$^+$. This virus was selected using tk$^-$ cells and HAT medium (Weir, et al., *Proc. Natl. Acad Sci. USA* 79: 1210–1214, 1982, hereby incorporated by reference and Example 4) to specifically select tk$^+$ virus plaques. DNA from a tk$^+$ plaque isolate, was analyzed by restriction endonuclease analysis (see FIG. 2B). The pattern of fragments generated by HindIII digestion of WR and vNotI/tk DNA were indistinguishable from one another whereas a double digestion with HindIII and NotI enzymes indicated that the NotI site was in the HindIII F fragment of WR and the HindIII J fragment of vNotI/tk).

Restriction endonuclease analysis of vNotI/lacZ/tk and vNotI/tk DNA: DNA was isolated from purified viral particles, digested with restriction enzymes and electrophoresed through a 0.8% agarose gel. The samples were, in FIG. 2A, from left to right: vNotI/lacZ/tk and WR DNAs cleaved with HindIII (H) and, WR and vNotI/lacZ/tk DNAs cleaved with HindIII and NotI (H/N). The position of the HindIII fragments are indicated on the left hand side. Prolonged electrophoresis (not shown in this photograph) revealed a mobility difference between the HindIII F fragments in WR and vNotI/lacZ/tk DNA when digested with HindIII and NotI. The fragment in vNotI/lacZ/tk corresponding to HindIII J was larger due to the additional sequences from the lacZ insert and migrated with the HindIII H fragment. Upon digestion with HindIII and NotI the larger portion of the fragment was detected between the HindIII I and HindIII H fragments. The samples were in FIG. 2B, from left to right: lambda, vaccinia WR, and vNotI/tk DNA cleaved with HindIII (H) WR and vNotI/tk DNA cleaved with HindIII and NotI (H/N). The arrowheads point to the location of the HindIII F and HindIII J fragment.

EXAMPLE 3

Transfection Procedure and Homologous Recombination

Plasmids containing genes or nucleic acid to be inserted into the target vaccinia genome were flanked by DNA from sites having homology to the regions of DNA flanking the target site for recombination on the vaccinia genome. The insert was incorporated into the vaccinia virus genome by homologous recombination. Typically, confluent monolayers of CV-1, BSC-1, TK 143 (all available from American Type Culture Collection (ATCC), Rockville Md.), or other cells in bottles with a 25 cm$^2$ bottom surface area were infected with 0.01 to 0.05 plaque forming units (pfu) per cell of vaccinia virus. Approximately 5 μg of plasmid DNA with or without carrier DNA (preferably appropriate viral DNA) was mixed in 1 ml of 0.1% dextrose, 0.14M NaCl, 5 mM KCl, 1 mM Na$_2$HPO$_4$, 20 mM Herpes, (pH 7.05) and precipitated by addition of CaCl$_2$ to a final concentration of 125 mM. The mixture was agitated gently and allowed to remain at room temperature for about 30 min. Two hr after infection, 0.8 ml of the fine suspension was added to an infected monolayer overlayed with 5 ml of media. After 4 hr., cell media was replaced with 5 ml of Eagle or other tissue culture medium containing 8% fetal bovine serum was added to each bottle and the incubation was continued at 37° C. for 48 more hr. At this time, the infected cells were scraped off the bottle, centrifuged, resuspended in tissue culture medium and lysed by three cycles of freeze thaw to liberate virus.

EXAMPLE 4

Thymidine Kinase (tk) Selection

When the nucleic acid fragment was inserted into the tk gene of virion DNA and the recombinants exhibited a tk negative (tk$^-$) phenotype. Selective conditions for isolation of tk- vaccinia virus were achieved by plaquing the virus in monolayers of tk$^-$ negative cells such as TK$^-$143 cells (American Type Culture Collection, Rockville, Md.) with 25 μ/ml of 5-bromodeoxyuridine (BUdR) in the 1% low melting agar overlay. After 48 to 72 hr at 37° C. in a 5% Co$_2$ humidified atmosphere, plaques were detected by staining with 0.005% neutral red.

EXAMPLE 5

DNA—DNA Hybridization

DNA.DNA hybridization was used to identify plaques formed by recombinant virus. In these procedures, virus was obtained following the methods of this invention, from infected cell monolayers with a 1% agar overlay. 48 to 72 hr postinfection, the plaques were detected by staining with neutral red. Isolated plaques were picked using a sterile Pasteur pipette and used to infect cell monolayers in 16 mm diameter wells of microtiter dishes. After a 48 hr incubation at 37° C., the cells were scraped, lysed by three freeze-thaw cycles, and collected on nitrocellulose sheets by filtration using a micro-sample manifold (Schleicher and Schuell, N.H.). Similarly, virus was isolated from infected cells (see *Current Protocols* pp. 16.183–16.18.4), digested with the appropriated restriction endonuclease, here HindIII or NotI and loaded onto 0.8% agarose gels and separated by electrophoresis. The nucleic acid was transferred to Nitrocellulose using Southern transfer procedures (Maniatis et al., supra). In either case, the filters were washed with 100 mM NaCl, 50 mM Tris-HCl (pH 7.5), blotted three times on successive Whatman 3 MM papers saturated with (1) 0.5M NaOH, (2) 1M Tris-HCl (pH 7.5), and (3) 2×SSC (SSC is 0.015M NaCl, 0.015M sodium citrate), baked at 80° C. for 2 hr and then incubated with 5×Denhardt's solution [Denhardt, *Biochem. Biophys. Res. Commun.*, 23: 641–646 (1966)], supplemented with 0.1 mg/ml of denatured salmon sperm DNA in 4×SSC at 65° C. for 4 hr. Suitable probe DNA was labeled with $^{32}$P by nick translation or end labelled with $^{32}$P-γATP. The probe was hybridized to the filter. The filters were washed at least twice for 15 min at 65° C. with 2×SSC/0.1% SDS (sodium dodecyl sulfate) and then with 0.2×SSC/0.1% SDS. An autoradiograph was made by placing the filter next to X-ray film. Another method of DNA.DNA hybridization used was described by Villarreal and Berg (*Science* 196: 183–185, 1977 hereby incorporated by reference). In this method, a replica of virus plaques was made by placing a nitrocellulose filter directly on the cell monolayer. DNA.DNA hybridization was carried out as above and, after location of plaques containing recombinant virus, residual virus was eluted from the agar that originally overlaid the plaques.

Additional methods that depend on expression of the foreign gene were also used to identify plaques. In one case, $^{125}$I-labeled antibodies to the product of the foreign gene were incubated with the cell monolayer containing virus plaques. Plaques containing recombinant virus were then identified by autoradiography.

EXAMPLE 6

Plaque Purification

After identification of vaccinia virus recombinants, 2 or more successive plaque purifications were carried out to obtain pure recombinant virus. Susceptible cells such as BSC-1, HeLa, MRC-5, or others were infected to obtain large stocks of recombinant virus. The titers of the stocks were determined by serial dilution and plaque assay.

EXAMPLE 7

Use of the Unique-Restriction Endonuclease Site Containing Vectors to Generate Recombinant Vectors by Direct In Vitro Ligation To establish the utility of the new cloning system of this invention, DNA was purified from vNotI/lacZ/tk or vNotI/tk and cleaved with NotI to produce arms of approximately 40 and 150 kbp. In separate experiments, two different size foreign DNA fragments with NotI ends were ligated to the vaccinia virus DNA arms. The first fragment of 4.3 kbp was obtained from pNot, a plasmid produced by digestion of pBR322 with HindIII, treatment with the Klenow fragment of DNA polymerase to fill in the recessed ends, and ligation to NotI linkers. The second fragment, of 26 kbp, was obtained from pBHL, a plasmid containing the HindIII B and L fragments from *Varicella zoster* virus (Davison, et al., *J. Gen. Virol* 67: 1759–1816, 1986 hereby incorporated by reference) cloned into pTR262 (Roberts, et al., *Gene* 12: 123–127, 1980 hereby incorporated by reference). This plasmid contained a single NotI site within the *Varicella zoster* coding sequence. The plasmids were digested with NotI, ligated separately to the vaccinia virus DNA arms at molar ratios of 4:1, and precipitated with calcium phosphate. It should be understood that other molar ratios may similarly be used, and optimum ratios will depend on the size of the arms relative to the size of the insert.

The precipitated DNA was applied to monolayers of CV-1 cells (ATCC) that had been infected 2 h earlier at a multiplicity of 0.05 with ts42, a conditionally lethal temperature sensitive vaccinia virus mutant that is defective in DNA replication (Condit, et al., *Virology* 128: 429–443 (1983); Sridhar, et al., *Virology* 128: 444–457 (1983) and Traktman, et al., *J. Virol* 63: 841–846 (1989) all hereby incorporated by reference) and homologous recombination (Merchlinksky, *J. Virol* 63: 2030–2035 (1989), hereby incorporated by reference) at 40° C. After incubation at 40° C. for 2 days, the cells were harvested and the virus titer was determined by plaque assay on cell lines at 37° C.

The progeny from those experiments using vNotI/tk were inoculated at 37° C. either onto BSC-1 cells in regular medium or tk$^-$ cells in selective medium following the techniques outlined in Example 4 and/or those described in *Current Protocols*. In contrast, virus formed by religation of the vaccinia virus arms or from helper virus would be tk$^+$ and consequently unable to form plaques under the selection conditions. Virus from plaques derived from vNotI/tk were inoculated onto BSC-1 cell monolayers, the DNA was isolated and immobilized on nitrocellulose membranes and hybridized to labeled DNA probes using methods provided in Example 5. Without selection, 7 out of 24 tested pNot-derived plaques and 6 out of 24 pBHL-derived plaques contained the appropriate insert DNA. With selection, all tested plaques (5 from pNot and 12 from pBHL) contained the expected insert.

Figure 4A:
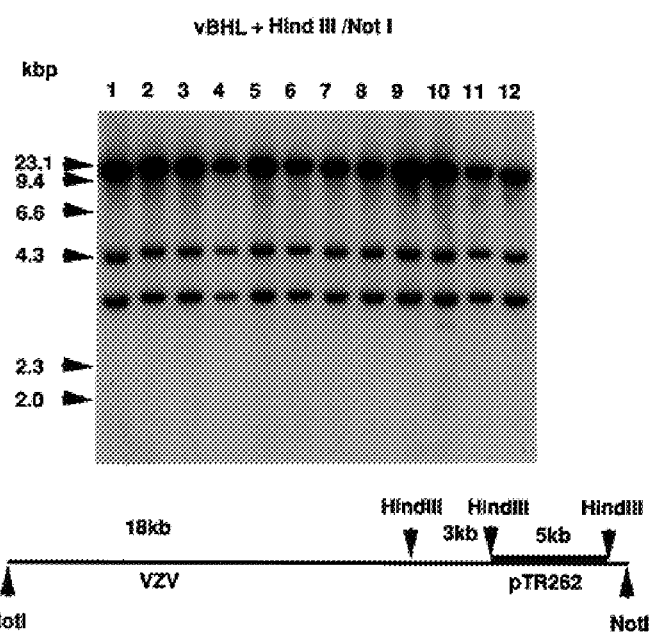
FIG. 4 illustrates the use of Southern blot analysis of vNotI/tk viral genomes to identify inserts derived from pBHL.
Figure 4B:
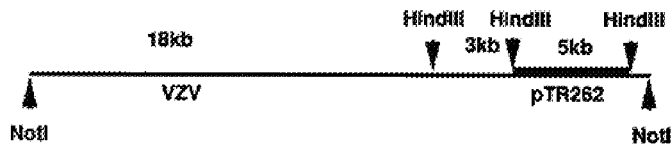
Figure 5:
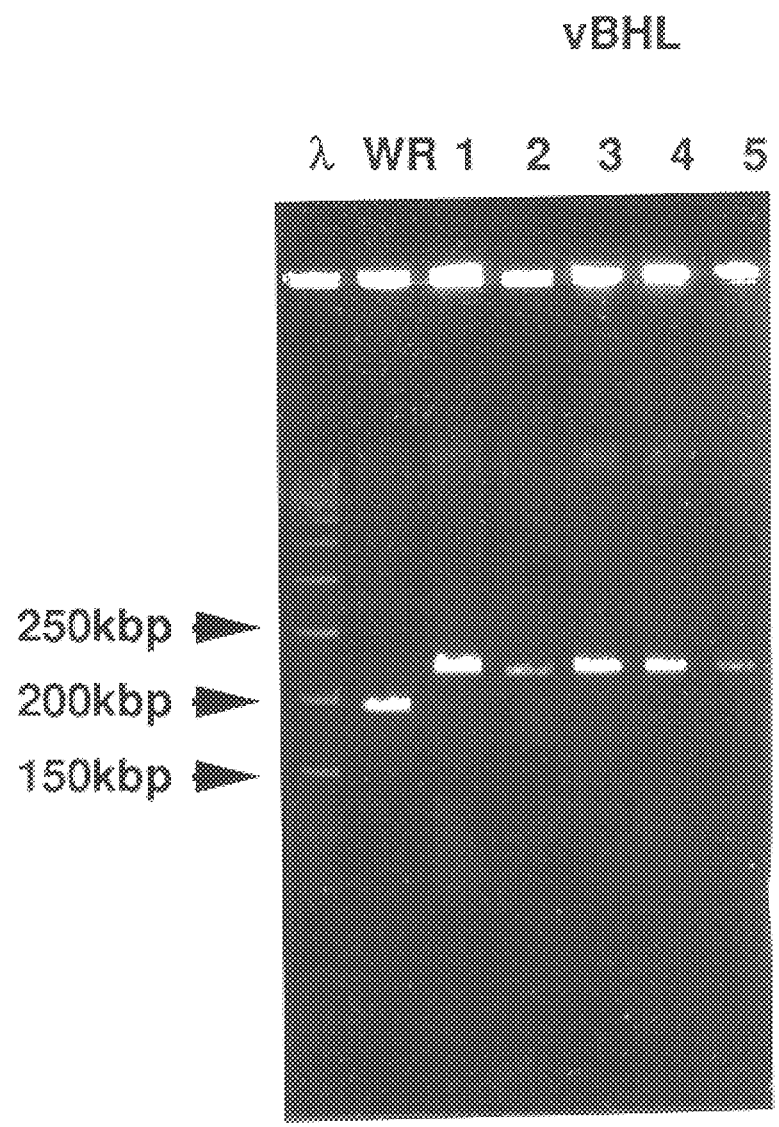
FIG. 5 is a photograph of a transverse alternating field electrophoresis gel (TAFE) comparing the electrophoretic pattern of vaccinia vector vNotI/tk DNA containing insert with wild type vaccinia.

NotI and HindIII double digests of DNA samples from cells infected with virus derived from the 12 plaques containing the BHL fragment isolated under BUdR selection were also analyzed by Southern blotting (FIG. 4 and Example 5). BSC-1 cells were infected with virus derived from the plaques isolated on tk$^-$ cells in the presence of bromodeoxyuridine after transfection with the ligation mix of vNotI/tk arms and the pBHL NotI fragment. DNA was isolated from cells using the methods of (Merchlinksky, et al., *J. Virol* 63: 1595–1603 (1989), hereby incorporated by reference) and analyzed by digestion with HindIII and NotI. The samples were electrophoresed through a 1.0% agarose gel, transferred to a nylon membrane (Nitrocellulose, Schleicher and Schuell) and probed by Southern blot hybridization (see Example 5) using pBHL DNA labeled with $^{32}$P by random primer extension (Pharmacia, Piscataway, N.J.).

The filter was visualized by autoradiography. The position of the fragments derived from a HindIII digestion of lambda DNA is shown on the left side where kbp refers to kilobase pairs. The lower portion of the figure is a representation of the pBHL plasmid after digestion with NotI and HindIII. The rightmost HindIII-NotI fragment is approximately 0.3 kilobases and has migrated off the gel. Three DNA fragments of 18, 5, and 3 kbp hybridized to the $^{32}$P-labeled pBHL probe suggesting that in each case the entire insert had been stably integrated into the vaccinia virus genome.

The latter interpretation was verified by electrophoresis and Southern blotting of the full length viral genomes from 5 of the plaque isolates (FIG. 5 and Example 5). BSC-1 cells were infected with virus derived from the plaques isolated on tk$^-$ cells in the presence of bromodeoxyuridine after transfection with the ligation mix of vNotI/tk arms and the pBHL NotI fragment. The cells were harvested into agar plugs (Merchlinksky, et al., *J. Virol* 63: 1595–1603 (1989) supra) and the DNA was electrophoresed through a TAFE (transverse alternating field electrophoresis) gel apparatus (Beckman) using a 1.0% agarose gel at 220 volts for 21 hours at 130 with a switching time of 15 seconds. The gel contained from left to right: lambda DNA, DNA derived from cells infected with vaccinia virus, and five lanes of DNA derived from cells infected with viruses derived from ligation of the pBHL fragment and vNotI/tk arms. In each case the DNA migrated more slowly than that of the nearly 200,000 bp wild type vaccinia virus WR genome, consistent with the insertion of an additional 26 kbp of DNA.

The transfection mix derived from vNotI/lacZ/tk was analyzed by plaque assay on BSC-1 cells at 37° C. Approximately one in thirty plaques were colorless. The virus from each of the colorless plaques analyzed (seven from the pNot ligation and six from the pBHL ligation) were shown to contain the correct DNA insert by restriction endonuclease analysis and Southern blotting. The absence of the NotI site in the HindIII F fragments of the chimeric genomes and the absence of a ts phenotype argue against recombination between transfected and helper virus DNA. For the small and large DNA fragments, approximately 300 and 100 colorless and 30 and 100 BUdR resistant plaques were obtained per microgram of vNotI/lacZ/tk or vNotI/tk DNA, respectively.

EXAMPLE 8

Generation of Herpesvirus Viral Vectors

The techniques for developing Herpesvirus (HSV) vectors follow the techniques outlined generally above. Many genes of HSV have been mapped to the viral genome. For a general review of the genome map with references see Roizman et al., "Herpes Simplex Viruses and Their Replication" in *Fundamental Virology,* Fields et al., eds. 1990, Raven Press, hereby incorporated by reference. Protocols are available for the site-specific insertion and deletion of nucleic acid inserts into the HSV genome by homologous recombination (Post et al., *Cell* 25: 227–232, 1981, and Roizman et al., *Science* 229: 1208–1214 (1985), both hereby incorporated by reference). In addition, a number of non-essential regions of the HSV genome have been identified. For a review of these regions see Roizman et al. in *Fundamental Virology,* supra. p. 860. Therefore, using site-directed mutagenesis, a technique well known in the art and available in kit form from manufacturers such as BioRad (Richmond, Calif.) or the like, a unique NotI restriction endonuclease site is inserted into the Herpesvirus thymidine kinase gene cloned into a plasmid suitable for homologous recombination with the HSV genome (see Poffenberg et al., *Proc. Natl. Acad. Sci. USA* 80: 2690–2694 (1983), hereby incorporated by reference). Other NotI sites located within the HSV genome are modified in non-essential portions of the genome by homologous recombination with plasmids containing the NotI site deleted by methods known in the art such as by cleaving the site, filling in with Klenow, and religating, as described in Example 1 and 2. For essential regions of the genome, the NotI site is modified by site-directed mutagenesis of plasmid fragments corresponding to sequences within essential regions of the genome followed by homologous recombination. Care is taken to ensure that the open reading frames of the essential portion of the genome are not interrupted by the deletion of the NotI sites.

Recombinants containing unique NotI sites within the thymidine kinase gene are isolated and verified by methods known in the art such as Southern analysis, by Polymerase Chain Reaction, or by DNA sequencing. Purified HSV genomes (see McGeoch et al., *J. Gen Virol.* 69: 1531–1574 (1988), hereby incorporated by reference) generated by the methods of this invention are cleaved with NotI to generate virus arms. The arms are ligated with a 4.3 kbp fragment from pNot modified to express *Varicella zoster* virus (VZV) protein (see Example 7) from a HSV genome. Ligated HSV is transfected into skin fibroblast cells (SF, ATCC) and cell lysates are screened for VZV protein expression on Western blots.

Those with skill in the art will recognize that further modifications to the HSV genome will be required to ensure that the virus produced from the recombinant HSV genomes of this invention have sufficiently reduced virulence characteristics before the recombinant virus enters vaccine trials.

EXAMPLE 9

Foreign Gene Expression

To express the foreign genes from the recombinant virus obtained from direct in vitro ligation, cells were infected with 1 to 30 pfu/cell of crude or purified virus and incubations were carried out at 37° C. for up to 48 hr. The foreign gene product, depending on its nature, was found in the cell culture medium or within the cells. When present in the cells, it was liberated by one of a number of methods, including sonication, freeze-thawing, homogenization or detergent treatment. The foreign protein was detected by immunological, enzymatic and electrophoretic methods known to those with skill in the art.

For infection of animals, recombinant virus are introduced intradermally, although other routes should be satisfactory. Formation of antibodies to the product of the foreign gene indicates that the foreign protein was made and was immunogenic.

While particular embodiments of the invention have been described in detail, it will be apparent to those skilled in the art that these embodiments are exemplary rather than limiting, and the true scope of the invention is that defined in the following claims.

What is claimed is:

1. A method of producing recombinant vaccinia viral particles having DNA inserted into the virus genome, comprising the following steps:
    cutting a purified vaccinia virus genome DNA at a single restriction endonuclease recognition site to produce a first arm and a second arm;
    ligating in vitro said first arm to a first end of an insert DNA and ligating said second arm to a second end of said insert DNA;
    introducing the ligated DNA into a host cell infected with a helper vaccinia virus; and
    recovering recombinant viral particles containing said insert DNA.

2. The method of claim 1, wherein said restriction endonuclease recognition site is located in a region of said vaccinia virus that is non-essential for replication of said vaccinia virus.

3. The method of claim 1, wherein the cutting step comprises complete digestion of said DNA with a restriction endonuclease that recognizes said single restriction endonuclease recognition site.

4. The method of claim 1, wherein said single restriction endonuclease recognition site is located within a marker gene associated with a phenotype, said method additionally comprising identifying viral arms containing insert DNA by identifying a change in phenotype.

5. The method of claim 1, wherein the helper virus is conditionally lethal.

6. The method of claim 5, wherein the helper virus does not allow replication of viral DNA in the presence of a functional thymidine kinase gene.

7. The method of claim 1, wherein said helper has a genome and the transfected DNA replicates essentially without recombination with the genome of the helper virus.

8. A vaccinia viral vector comprising:
    a vaccinia virus genome containing a unique restriction endonuclease recognition site; and
    an exogenous marker gene, said unique restriction endonuclease recognition site being within said marker gene and within a region of said genome that is nonessential for replication of said vector.

9. The vector of claim 8, wherein said marker gene comprises a gene coding for a protein, such that the presence of insert DNA in said unique restriction endonuclease recognition site can be detected upon growth of said vector in a host cell that permits transcription of said DNA sequence by detecting absence of function of the marker protein.

10. The vector of claim 9, wherein said protein is viral thymidine kinase.

11. The vector of claim 8, wherein said single restriction endonuclease site is a NotI site.

12. The vector of claim 8, wherein said vector is cleaved at said single restriction site.

13. A method of producing recombinant vaccinia viral particles having DNA inserted into the virus genome, comprising the following steps:
    purifying a vaccinia virus genomic DNA comprising a plurality of restriction endonuclease recognition sites;
    methylating all but one of said restriction endonuclease recognition sites thereby creating a single unmodified restriction endonuclease recognition site that can be cut by a restriction endonuclease recognizing said site;
    cutting said purified vaccinia viral genomic DNA at said single restriction endonuclease recognition site to produce a first arm and a second arm;

ligating in vitro said first arm to a first end of an insert DNA and ligating said second arm to a second end of said insert DNA;

introducing the ligated DNA into a host cell infected with a helper vaccinia virus; and recovering recombinant viral particles containing said insert DNA.

14. The method of claim 13, wherein said unmodified restriction endonuclease recognition site is located in a region of said vaccinia viral genomic DNA that is non-essential for replication of said vaccinia virus.

15. The method of claim 13, wherein said unmodified restriction endonuclease recognition site is located within a marker gene associated with a phenotype, said method additionally comprising identifying viral arms containing insert DNA by identifying a change in said phenotype.

16. A method of producing recombinant vaccinia viral particles having DNA inserted into the virus genome, comprising the following steps:

obtaining a vaccinia virus having a genomic DNA comprising a plurality of restriction endonuclease recognition sites;

adding, deleting, or changing a base within all but one of said restriction endonuclease recognition sites thereby creating a single unmodified restriction endonuclease recognition site that can be cut by a restriction endonuclease recognizing said site;

purifying the vaccinia viral genomic DNA;

cutting said purified vaccinia viral genomic DNA at said single restriction endonuclease recognition site to produce a first arm and a second arm;

ligating in vitro said first arm to a first end of an insert DNA and ligating said second arm to a second end of said insert DNA;

introducing the ligated DNA into a host cell infected with a helper vaccinia virus; and recovering recombinant viral particles containing said insert DNA.

17. The method of claim 16, wherein said unmodified restriction endonuclease recognition site is located in a region of said vaccinia viral genomic DNA that is non-essential for replication of said vaccinia virus.

18. The method of claim 16, wherein said unmodified restriction endonuclease recognition site is located within a marker gene associated with a phenotype, said method additionally comprising identifying viral arms containing insert DNA by identifying a change in said phenotype.

19. The method of claim 16, wherein said adding, deleting, or changing a base comprises homologous recombination with a DNA sequence containing an added, deleted, or changed base.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Vaccinia Virus
        ( C ) INDIVIDUAL ISOLATE: tk gene oligonucleotide probe ( x i ) SEQUENCE DESCRIPTION: SEQ ID NO:1:

A T G T C C G C C G    T T G G C G G C C G    C C A T G A T G A C    A A T A A A        3 6

( 2 ) INFORMATION FOR SEQ ID NO:2:

```
        ( i ) SEQUENCE CHARACTERISTICS:
               ( A ) LENGTH: 51 bases
               ( B ) TYPE: nucleic acid
               ( C ) STRANDEDNESS: single
               ( D ) TOPOLOGY: linear ( i i ) MOLECULE TYPE: DNA (genomic)

( i i i ) HYPOTHETICAL: NO ( v i ) ORIGINAL SOURCE:
               ( A ) ORGANISM: vNotI/lacZ/tk plasmid
               ( C ) INDIVIDUAL ISOLATE: beta- galactosidase gene ( x i ) SEQUENCE DESCRIPTION: SEQ ID NO:2:

ATGGTTCGTA  ACAAACGCAA  CGAGGCTCTA  CGAATCGGGG  ATCGCGGCCG  C                    5 1

( 2 ) INFORMATION FOR SEQ ID NO:3:

( i ) SEQUENCE CHARACTERISTICS:
               ( A ) LENGTH: 21 base pairs
               ( B ) TYPE: nucleic acid
               ( C ) STRANDEDNESS: single
               ( D ) TOPOLOGY: linear ( i i ) MOLECULE TYPE: DNA (genomic)

( i i i ) HYPOTHETICAL: NO ( v i ) ORIGINAL SOURCE:
               ( A ) ORGANISM: vNotI/tk plasmid
               ( C ) INDIVIDUAL ISOLATE: thymidine kinase gene ( x i ) SEQUENCE DESCRIPTION: SEQ ID NO:3:

ATGGCGGCCG  CCAACGGCGG  A                                                        2 1
```